United States Patent [19]

Cook

[11] Patent Number: 4,929,420

[45] Date of Patent: May 29, 1990

[54] ALLOY USEFUL PARTICULARLY IN DENTISTRY

[75] Inventor: Peter Cook, Horstead, England

[73] Assignee: The National Research Development Corporation, London, England

[21] Appl. No.: 300,509

[22] Filed: Jan. 23, 1989

[30] Foreign Application Priority Data

Jan. 23, 1988 [GB] United Kingdom ............... 8801532

[51] Int. Cl.$^5$ .............................................. C22C 5/04
[52] U.S. Cl. .................................... 420/466; 428/457; 428/469; 433/207; 433/222.1
[58] Field of Search .................. 420/466, 467, 468; 433/207, 218, 222.1, 223; 428/457, 469

[56] References Cited

U.S. PATENT DOCUMENTS 4,806,306 2/1989 Groll et al. ........................ 420/467

FOREIGN PATENT DOCUMENTS 210936 12/1982 Japan ................................. 420/467

*Primary Examiner*—Robert McDowell
*Attorney, Agent, or Firm*—Cushman, Darby & Cushman

[57] ABSTRACT

The invention provides an alloy useful particularly in dentistry.

The alloy of the invention in its broadest aspect contains from about 0.05 to about 8% by weight of indium and from about 8 to about 20% by weight of iridium, the balance essentially being platinum. Preferably, however, the allow consists essentially of platinum, iridium and indium, and contains from about 0.05 to about 8% by weight of indium, with the weight ratio of platinum to iridium being from about 84 to about 86:15.

The alloy is useful in forming dental prostheses with aluminous porcelain or with a castable ceramic.

11 Claims, No Drawings

ALLOY USEFUL PARTICULARLY IN DENTISTRY

BACKGROUND TO THE INVENTION (a) Field of the invention

The present invention relates to a novel alloy, useful particularly in dentistry.

(b) Description of the Prior Art

Two types of porcelain are used to form artificial teeth or parts thereof to fix to abutments (fashioned stumps) of natural teeth in the patient's mouth. These two types are aluminous porcelain and feldspatic porcelain. Aluminous porcelain is generally regarded as superior, in matching the look of live teeth, in being more workable, in being stronger and in being not as hard. The hardness of aluminous porcelain is more like that of natural teeth and hence in use it does not abrade natural teeth as much as feldspatic porcelain. Aluminous porcelain is thus much used for cementing directly to abutments by means of a cement.

Feldspatic porcelain, however, is used for bonded work. That is to say in the case where the porcelain is fused to a cast metal substructure, thereby effecting a bond between the two materials, and the substructure is then cemented to the abutment. Feldspatic porcelain is little used for non-bonded work because of the superiority of aluminous porcelain.

On the other hand, aluminous porcelain is not used for bonded work because there is no metal known from which there may be formed a compatible cast metal substructure. Thus, while aluminous porcelain would be preferred for bonded work were there to be a metal known from which a compatible cast metal substructure could be formed, no such material is known. There is, therefore, a need for a metallic material for use in forming such substructures.

OBJECTS OF THE INVENTION

It is one object of the present invention to provide a metallic material for use in forming a substructure compatible with aluminous porcelain.

Another object of the present invention is to provide an alloy which permits aluminous porcelain to be used in bonded work.

Yet another object of the present invention is to provide an alloy which is very workable and which can be used in a simple manner to form dental prostheses with aluminous porcelain.

In accordance with the foregoing objects I have now found surprisingly that a highly suitable metallic material which enables the excellent properties of aluminous porcelain to be employed in bonded work can be prepared as an alloy of platinum, iridium and indium.

Accordingly, the present invention in one aspect provides an alloy consisting essentially of platinum, iridium and indium, which contains from about 0.05 to about 8% by weight of indium and whose weight ratio of platinum to iridium is from about 84 to about 86:15.

DESCRIPTION OF THE INVENTION

The alloy of the present invention, unlike those presently used for bonding to feldspatic porcelain, has a linear coefficient of expansion similar to that of aluminous porcelain, which is of the order of about 7.5 $\times 10^{31\ 6}$ per °C. Consequently, the alloy can be fired with aluminous porcelain to bond thereto. In contrast, feldspatic porcelain, and hence the alloys used for bonding feldspatic porcelain, have a much higher linear coefficient of expansion. This makes such alloys useless for bonding to aluminous porcelain.

The alloy of the present invention is very workable and can be used in a simple manner to form dental substructures and to form dental prostheses with aluminous porcelain. The alloy has good physical properties and bonds well. It can be used with standard dental laboratory equipment and can be employed in techniques similar to those standardly used for feldspatic porcelain and alloys used with such porcelain.

The alloy of the present invention is of high clinical safety. It is based on platinum, iridium and indium, and generally does not contain allergens such as nickel or beryllium.

It can be seen that such properties make the alloy of the present invention remarkably useful for bonding to aluminous porcelain in dentistry. Although this is seen at present as the main use of the alloy, it can also be envisaged as useful in other applications where its properties, including its resistance to heat or corrosive gases, are useful or desirable, for example, in electrical contacts.

The alloy of the present invention is silver in colour. It is believed that it is the specifically chosen ratio of platinum to iridium in the alloy which achieves the desired coefficient of expansion, so that the alloy can be bonded to aluminous porcelain. This ratio is from about 84:15 to about 86:15 by weight, and preferably is about 85:15 by weight. It has been found that for the purpose of the present invention the alloy should be formed with the said ratio in the given very narrow range, at least essentially as stated above. However, the indium content is less critical, and serves the purpose of acting as bonding agent, as well as lowering the melt point of the alloy to facilitate its casting and working in a standard dental laboratory. The content of indium is from about 0.05 to about 8%, preferably from about 2 to about 7%, and especially from about 5 to about 6% by weight.

Although the alloy consists essentially of the above-mentioned three essential ingredients, very small amounts, e.g. up to about 1% by weight in total, of other alloying ingredients may be present providing they do not alter the essential nature of the alloy, namely its ability to be bonded to aluminous porcelain. For example, the alloy may contain up to about 0.5% of weight of tin, though this is not preferred.

The ratios and percentages herein are based on pure ingredients. However, impurities may be present, again providing they do not alter the essential nature of the alloy. Thus, for example, commercially available ingredients may be employed and a small percentage of iron, say up to about 1.5% by weight, and a small percentage of chromium, say up to about 0.5% by weight, may be present as impurities, and typically may be introduced as impurities in the iridium used to form the alloy. Also, a small amount of boron of up to about 0.5%, e.g. about 0.3% by weight, may be included to lower the melting point slightly, the boron being gassed out after the alloy is heated and cast.

In addition, use of the alloy may have other effects on its constitution. Thus, in use there may be a small loss of indium due to gassing which may increase as the alloy is used and the alloy is melted a number of times. Also, perhaps due to differential cooling effects, as well as losses on melting, the alloy once used may analyse at different points in a block of alloy to provide a ratio of platinum to iridium which is outside the above-mentioned range.

For example, an alloy prepared from 8.5 g of platinum, 1.5 g of iridium and 0.6 g of indium analysed after being cast twice to give in the extreme ratios of platinum to iridium of between about 125:15 and about 70:15, with figures of about 100:15 and about 90:15 within that range. Also, the indium content varied between about 3.3 and about 1.8% by weight. Thus, the ratio of from about 84 to about 86:15 as given herein to be essential in the alloy of the invention is essential in the sense that it is the ratio at which the alloy is mixed. It is not necessarily the ratio to be found in the alloy after use. Furthermore, the same may be true for the indium content.

Accordingly, in its broadest aspect the invention provides an alloy, which alloy contains from about 0.05 to about 8% by weight of indium and from about 8 to about 20% by weight of iridium, the balance essentially being platinum. Preferably, in such an alloy the amount of iridium is from about 9 to about 17% by weight, for example, from about 10 to about 15% by weight.

The alloy of the present invention is preferably prepared by melting the platinum and iridium together to form a platinum/iridium alloy, cooling to solidify the platinum/iridium alloy, melting the platinum/iridium alloy with indium to form a platinum/iridium/indium alloy, and cooling to solidify the platinum/iridium/indium alloy. In that manner the indium can be introduced at a lower temperature, which is advantageous to avoid it volatilizing. The alloying can be done using an oxypropane flame in air.

Thus, the present invention includes a process for preparing an alloy in accordance with the invention, which process comprises melting platinum and iridium together to form a platinum/iridium alloy, cooling to solidify the platinum/iridium alloy, melting the platinum/iridium alloy with indium to form a platinum/iridium/indium alloy, and cooling to solidify the platinum/iridium/indium alloy.

The alloy of the present invention generally may be used to form a bonded structure with aluminous porcelain. Accordingly, the invention also includes a bonded structure, which structure comprises aluminous porcelain bonded to an alloy.

Preferably, however, the alloy is cast into a dental substructure of the alloy. Thus, it is preferably used to form a dental prosthesis comprising a cast substructure of the alloy, which substructure is adapted to fit onto at least one corresponding abutment of a natural tooth in the patient's mouth, to which substructure is bonded aluminous porcelain in the shape and size of a tooth, teeth or part of a tooth, and the invention includes such a prosthesis.

It will be appreciated that except for the use of the alloy of the present invention and aluminous porcelain, the above prosthesis is of a known form. Thus, the prosthesis can be prepared in a standard manner by taking an impression of an abutment or abutments in a patient's mouth, forming a cast model from that impression, casting the alloy to form the substructure from that cast model, building on that substructure, with a mix of aluminous porcelain powder and water, a prosthesis of the desired shape and size, and firing to bond the aluminous porcelain to the substructure and hence to form the finished prosthesis. However, although such a technique is known, it is included as part of the present invention insofar as it uses the novel alloy of the invention.

The prosthesis made using the alloy of the invention is preferably a crown or a bridge, but it may be an inlay—in which case part, usually most, of the abutment of the patient's natural tooth is left exposed when the inlay is cemented in place. Thus, preferably the prosthesis is a dental crown or bridge comprising a coping of the alloy of the invention, to which coping is bonded aluminous porcelain in the shape and size of a tooth or teeth. The crown may be a jacket crown (where the abutment on which the crown fits is a stump fashioned entirely from a natural tooth) or a post crown (where the abutment on which the crown fits is a post embedded in the root of a natural tooth).

The substructure can be prepared in the standard way as follows:

An impression in the patient's mouth is taken using impression material, for example, a silicone, and a cast model is made from that impression, thus reproducing the shape and size of the relevant portion of the mouth in which the prosthesis is to fit. A pattern reproducing the shape and size of the required substructure is formed, suitably in wax, on the model. The pattern is invested in a refractory material, for example, a phosphate investment material e.g. "Hi-heat" (from Whipmix, a U.S. Company). The alloy is cast in the investment material, to form the basic substructure. This is trimmed and fitted onto the model, to form the substructure. As is standard, the substructure is then preferably heated in a furnace in air to produce a surface oxide, which helps to create the bond between metal and porcelain. On the substructure, the required shape and size of the prosthesis is built up using a mix of aluminous porcelain powder and water, desirably distilled water. Usually several different aluminous porcelain powders are employed. A first may be of a higher coefficient of expansion and optically more dense to form an inner jacket masking the colour of the alloy and preferably used at a thickness no greater than is required to achieve that purpose, and the substructure bearing the inner jacket is fired. After cooling, an aluminous porcelain of lower expansion coefficient and optically less dense is applied in the same way to form an outer jacket. The whole is then fired. Finally, an aluminous porcelain which forms an enamel veneer is applied in the same manner, and the whole fired to form the prosthesis. The porcelain is preferably Vitadur 'N' (an aluminous porcelain obtainable from Vita Zahnfabrik, H Rauter GmbH, a West German Company), which is a porcelain widely used to make all-porcelain jacket crowns. The firing, to bond the aluminous porcelain to the substructure, is preferably carried out under vacuum.

The prosthesis may be cemented into place on the abutment or abutments in the patient's mouth in a standard manner using, for example, a zinc oxyphosphate cement.

In the above general description, and in the more specific description which follows, the alloy of the invention is described as useful in conjunction with aluminous porcelain. However, as will be appreciated by those skilled in the art, the alloy of the invention may also be used with any other material which can be used to form a dental prosthesis and which has a coefficient of expansion which matches that of the alloy. For example, the alloy may be used with a castable ceramic such as the material known as Dicor (supplied by Dentsply, a U.S. Company). In such use, a substructure of the alloy is formed and the ceramic is then cast on the substructure to form a bridge or crown or the like. In accordance with such a more general use, the invention includes a bonded structure comprising a castable ceramic and the alloy of the invention.

DESCRIPTION OF THE PREFERRED EMBODIMENTS

The alloy of the present invention and its use are illustrated by the following specific Examples, percentages being by weight. The platinum was platinum foil "Red Ribbon" from the Scientific Metal Company, of London, England, the iridium was iridium sheet from Engelhard Ltd., of Chessington, England, and the indium was also from Engelhard.

EXAMPLE 1

An alloy was made by alloying 8.5 g of platinum with 1.5 g of iridium in air using an oxypropane flame. The two metals were heated until completely mixed, and then allowed to cool. The mix was re-heated and 0.6 g of indium was then heated and incorporated into the mix by heating until the indium was completely mixed into the melt. The melt was allowed to cool and the resulting alloy consisted of:

80.19% Pt, 14.15% Ir and 5.66% In.

The alloy was silver in colour. Its coefficient of linear expansion was assessed to be about $7.7 \times 10^{-6}$ per °C. (based on the Pt/Ir alloy being assessed as having a coefficient of about $7.3 \times 10^{-6}$ per °C., and this being increased by the indium).

EXAMPLE 2

A dental crown and a dental bridge were made from the alloy of Example 1 by the following technique, using the aluminous porcelain Vitadur 'N':

The model was constructed by methods standard in the dental laboratory. The wax form was made by the method standard in dental laboratories to form a crown or bridge. The sprueing and investment techniques were the same standard techniques as used in dental laboratories except that the phosphate investment was carbon free and a metal casting ring was not required.

The investment mould, when set, was pre-heated at 350° C. for hour and then raised to 800° C. over another hour. It was then raised to 1200° C. over the next hour and heat soaked for 10 minutes per 60 g per mass of investment. The casting was done in an E4 type centrifugal casting machine (made by Nessor, a British Company). The melt crucible was clean and free from any other alloys, and was pre-heated up to 800° C. When the alloy was placed in the machine and pre-heated to near the melt temperature, the mould was placed in the casting machine, the alloy melted until it was completely molten and the casting was then completed.

The cast was thereafter allowed to cool and was deflasked. The resulting casting was cleaned, fitted and trimmed by standard laboratory techniques, and formed the metal substructure on to which the aluminous porcelain was bonded.

The cast coping (the metal substructure) was first cleaned by boiling in distilled water for 5 minutes to degrease it. Then it was then placed in the furnace at 1060° C. for 5 minutes in air, in order to produce a surface oxide, which helps to create a bond between metal and porcelain. When cooled, the porcelain was applied. The core material, known as "Pt range", was mixed with distilled water and a thin coating applied to the surface of the metal substructure, sufficient to mask the metal colour but no thicker than was required to do this. The coated substructure was then fired for 6 minutes at 1060° C., 4 minutes of which was in air and 2 minutes in vacuum, and cooled in air. The enamel and dentine porcelains were then mixed with distilled water and applied in the standard manner, as in any dental laboratory, and fired under vacuum as is recommended by the manufacturers of Vitadur 'N'. The completion of the crown and bridge was carried out in the manner standard in the dental laboratory.

EXAMPLES 3 TO 7

Following the procedure of Example 1, alloys were prepared from the following ingredients:

| Example | Pt, g | Ir, g | In, g | Sn, g |
|---------|-------|-------|-------|-------|
| 3 | 8.5 | 1.5 | 0.05 | 0.02 |
| 4 | 8.5 | 1.5 | 0.125 | 0.05 |
| 5 | 8.5 | 1.5 | 0.4 | — |
| 6 | 8.5 | 1.5 | 0.8 | — |
| 7 | 8.6 | 1.4 | 0.6 | — |

EXAMPLES 8 TO 12

The alloys of Examples 3 to 7 were used to make a crown and a bridge following the procedure of Example 2. Each was satisfactory, but not as good as the alloy of Example 1, for the following reasons:

| Example | Using Alloy of Example | Results |
|---------|------------------------|---------|
| 8 | 3 | Melt point higher. Bond acceptable but not as good |
| 9 | 4 | Melt point higher. Alloy acceptable but more brittle |
| 10 | 5 | Melt point higher |
| 11 | 6 | Alloy acceptable but slightly more brittle |
| 12 | 7 | The multiple units of the bridge were not as well matched |

As will be appreciated, the invention is not limited to the details of the above specific Examples and numerous variations may be made within the ambit of the above general and specific description and the spirit and scope of the claims which follow.

I claim:

1. An alloy consisting essentially of platinum, iridium and indium, which contains from about 0.05 to about 8% by weight of indium and whose weight ratio of platinum to iridium is from about 84:15 to about 86:15.

2. An alloy according to claim 1, which contains from about 2 to about 7% by weight of indium.

3. An alloy according to claim 1, which contains from about 5 to about 6% by weight of indium.

4. An alloy according to claim 1, whose weight ratio of platinum to iridium is about 85:15.

5. An alloy made by alloying 8.5 parts by weight of platinum, 1.5 parts by weight of iridium and 0.6 parts by weight of indium.

6. An alloy, which alloy contains from about 0.05 to about 8% by weight of indium and from about 8 to about 20% by weight of iridium, the balance essentially being platinum.

7. An alloy according to claim 6, which contains from about 9 to about 17% by weight of iridium.

8. An alloy according to claim 6, which contains from about 10 to about 15% by weight of iridium.

9. A process for preparing an alloy according to claim 6, which process comprises melting platinum and iridium together to form a platinum/iridium alloy, cooling to solidify the platinum/iridium alloy, melting the platinum/iridium alloy with indium to form a platinum/iridium/indium alloy, and cooling to solidify the platinum/iridium/indium alloy.

10. A bonded structure, which structure comprises aluminous porcelain bonded to an alloy according to claim 6.

11. A bonded structure, which structure comprises a castable ceramic bonded to a substructure of an alloy according to claim 6.

* * * * *